United States Patent
Kleemann et al.

[11] Patent Number: 6,066,597
[45] Date of Patent: May 23, 2000

[54] HERBICIDAL 2-(HETERO)ARYLOXY-6-ARYLPYRIDINES AND 2-ARYL-4-(HETERO)ARYLOXY-6-ARYLPYRIDINES AND 2-ARYL-4-(HETERO)ARYLOXYPYRIMIDINES

[75] Inventors: Axel Kleemann, Königstein; Helmut Siegfried Baltruschat, Schweppenhausen; Thekla Haselwander, Weil am Rhein, all of Germany

[73] Assignee: American Cyanamid Company, Madison, N.J.

[21] Appl. No.: 09/361,906

[22] Filed: Jul. 27, 1999

Related U.S. Application Data

[62] Division of application No. 09/115,275, Jul. 14, 1998, which is a division of application No. 08/761,479, Dec. 6, 1996, Pat. No. 5,824,624, which is a continuation of application No. 08/454,044, May 30, 1995, abandoned.

[51] Int. Cl.[7] .................... C07D 401/12; A01N 43/40
[52] U.S. Cl. .................... 504/251; 504/253; 504/238; 504/242; 504/230; 546/276.1; 546/256; 544/219; 544/239; 544/333; 544/405
[58] Field of Search .................... 546/276.1, 261; 504/253, 251, 238, 242, 230; 544/219, 333, 405, 239

[56] References Cited

U.S. PATENT DOCUMENTS

| | | | |
|---|---|---|---|
| 3,576,616 | 4/1971 | Nowotny et al. | 504/256 |
| 3,637,720 | 1/1972 | Nishiyama et al. | 504/256 |
| 4,405,743 | 9/1983 | Nishimura et al. | 514/273 |
| 4,493,726 | 1/1985 | Burdeska et al. | 544/334 |

FOREIGN PATENT DOCUMENTS

| | | |
|---|---|---|
| 0263958-A1 | 4/1988 | European Pat. Off. . |
| 0354766-A2 | 2/1990 | European Pat. Off. . |
| 0425247-A1 | 5/1991 | European Pat. Off. . |
| 0572093-A1 | 12/1993 | European Pat. Off. . |
| 4029654 | 9/1990 | Germany . |
| 2131480A | 2/1989 | Japan . |

OTHER PUBLICATIONS

Inouye et al., Journal of Fluorine Chemistry, 27, pp. 231–236 (1985).

*Primary Examiner*—Jane Fan
*Attorney, Agent, or Firm*—Timothy J. Babcock

[57] ABSTRACT

New herbicidal pyridine and pyrimidine derivatives of general formula (I),

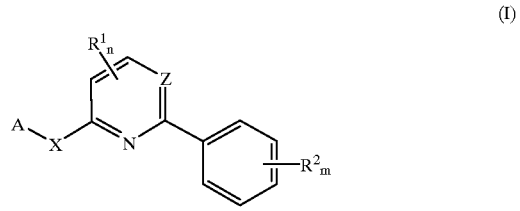

wherein Z represents a nitrogen atom or a C—H group; A represents an optionally substituted aryl group or an optionally substituted 5- or 6-membered nitrogen-containing heteroaromatic group; n represents an integer from 0 to 2 and $R^1$ or each $R^1$ independently represents a hydrogen atom or an optionally substituted alkyl, alkoxy, alkylthio or dialkylamino group; m represents an integer from 0 to 5 and $R^2$ or each $R^2$ independently represents a hydrogen or a halogen atom or an optionally substituted alkyl, haloalkyl, haloalkoxy, alkoxy, alkylthio group or a nitro, cyano or a halosulphonyl group; and X represents an oxygen or sulphur atom.

8 Claims, No Drawings

HERBICIDAL 2-(HETERO)ARYLOXY-6-ARYLPYRIDINES AND 2-ARYL-4-(HETERO)ARYLOXY-6-ARYLPYRIDINES AND 2-ARYL-4-(HETERO)ARYLOXYPYRIMIDINES

This is a divisional of copending application Ser. No. 09/115,275 filed on Jul. 14, 1998 the entire disclosure of which is hereby incorporated by reference which is a division of Ser. No. 08/761,479, filed Dec. 6, 1996, now U.S. Pat. No. 5,824,624 which is a continuation of Ser. No. 08/454,044 filed May. 30, 1995, now abandoned.

The present invention relates to certain 2,6-disubstituted pyridines and 2,4-disubstituted pyrimidines, their preparation and use as herbicides.

Pyridines, pyrimidines and their derivatives have many uses in the pharmaceutical area as well as in agriculture (herbicides, fungicides, acaricides, anthelmintics, bird repellents), reagents, intermediates and chemicals for the polymer and textile industry.

2-Arylpyrimidines and 2-pyrimidinyl-6-arylpyridines for example have been described as fungicides (DE 40 29 654 and JO 2131-480, respectively). EP 263,958 is concerned with herbicidal 2,6-diphenylpyridines, and structurally related 2,4-diphenylpyrimidines have been disclosed in EP 354,766 and 425,247, respectively, which are also said to be herbicides. Another example are 2,6-diphenoxypyridines, which have been published in EP 572,093 as herbicides. 4-Phenoxy-2-pyrazol-1-yl-pyrimidines are disclosed in DE 29 35 578 to have fungicidal activity. Huelsen (Diplomarbeit, Konstanz 1993) describes four distinct 2-(1-methyl-3-trifluoromethyl-pyrazol-5-ylyoxy)-6-phenyl pyridines, however, no biological activity is disclosed.

Surprisingly, it has now been found that good herbicidal activity is present in related, novel pyridine and pyrimidine derivatives having both an aryl group and an aryloxy or a heteroaryloxy group. These compounds unexpectedly show excellent activity and good crop selectivity in pre- and post-emergence applications on both broadleaf and grassy weed species.

Accordingly, the present invention provides 2,6-substituted pyridines and 2,4-substituted pyrimidines of the general formula I

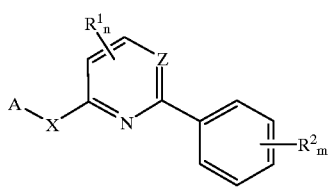

(I)

wherein Z represents a nitrogen atom or a C—H group; A represents an optionally substituted aryl group or an optionally substituted 5- or 6-membered nitrogen-containing heteroaromatic group; n represents an integer from 0 to 2 and $R^1$ or each $R^1$ independently represents a hydrogen atom or an optionally substituted alkyl, alkoxy, alkylthio or dialkylamino group; m represents an integer from 0 to 5 and $R^2$ or each $R^2$ independently represents a hydrogen or a halogen atom or an optionally substituted alkyl, haloalkyl, haloalkoxy, alkoxy, alkylthio group or a nitro, cyano or a halosulphonyl group; and X represents an oxygen or sulphur atom; with the proviso that when Z is C—H, A is 1-methyl-3 trifluoromethyl-pyrazol-5-yl, n is 0 and X is oxygen, then m must be other than 0 and when m is 1 then $R^2$ cannot be a 3-trifluoromethyl substituent and when m is 2, then $R^2$ cannot be a 2,4-dichloro substituent or a 2,4 dimethyl substituent.

An aryl group as substituent or part of other substituents is suitably an optionally substituted phenyl or naphthyl group. A 5- or 6-membered heteroaryl group comprises optionally substituted 5- or 6 membered heterocycles containing one or more nitrogen and/or oxygen and/or sulfur atoms, 1 to 3 nitrogen atoms being preferred. Example of such groups are pyrazolyl, imidazolyl, triazolyl, tetrazolyl, pyridyl, pyrazinyl, pyridazinyl and triazinyl groups.

Generally, when any of the above mentioned moieties comprises an alkyl group, this alkyl group, unless otherwise specified, may be linear or a branched and may suitably contain 1 to 12, preferably 1 to 4, carbon atoms. Examples of such groups are methyl, ethyl, propyl, isopropyl, isopropyl, butyl, isobutyl and tertiary-butyl groups. An alkyl portion of a haloalkyl, haloalkoxy, alkylthio or alkoxy group suitably has from 1 to 4 carbon atoms, preferably 1 or 2 carbon atoms.

Halogen represents a fluorine, chlorine, bromine or iodine atom. Haloalkyl and haloalkoxy are preferably mono-, di- or trifluoroalkyl and -alkoxy, especially trifluoromethyl and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each part of the molecules. In relation to moieties defined above as comprising an optionally substituted alkyl group, including alkyl parts of haloalkyl, alkoxy, alkylthio haloalkoxy and dialkylamino groups, specific examples of such substituents include phenyl, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine and nitro, cyano, amino, hydroxyl, $C_{1-4}$-alkyl, $C_{1-4}$-alkoxy, $C_{1-4}$-haloalkyl, $C_{1-4}$-haloalkoxy and halosulphonyl groups. 1 to 5 substituents may suitably be employed, 1 to 2 substituents being preferred.

The compounds according to general formula I are oils, gums, or, predominantly, crystalline solid materials. They can be used in agriculture or related fields for the control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, lpomoea purpurea* and *Amaranthus retroflexus* by pre- and post-emergence application. The compounds of general formula I according to the invention possess a high herbicidal activity within a wide concentration range and may be used in agriculture without any difficulties.

Preferred compounds are those wherein A represents a phenyl, pyridyl, or pyrazolyl group, being substituted by one or more identical or different substituents selected from halogen atoms, alkyl, alkoxy, haloalkyl, haloalkoxy and pentahalosulphonyl groups.

Especially preferred are compounds bearing a substituent in group A in meta-position relative to the point of attachment of this group.

Good results in terms of control of undesired plant growth are obtained when A is meta-substituted by a chlorine atom or a trifluoromethyl group, especially A being a 2-chloropyrid-4-yl, 1-methyl-3-trifluoromethylpyrazol-5-yl or 3-trifluoromethylphenyl group.

Particularly good results in control of weeds are achieved with compounds wherein X represents an oxygen atom.

Especially good results are obtained with compounds wherein Z represents a nitrogen atom.

Among the compounds exemplified by the invention are the following compounds:

2-(1'-methyl-3'-trifluoromethylpyrazol-5'-yloxy)-6-(4"-trifluoromethylphenyl)pyridine, 2-(2',4'-difluorophenyl)-6-methyl-4-(1"-methyl-3"-trifluoromethylpyrazol-5"-yloxy)pyrimidine, 2-(2',4'-difluorophenyl)-6-methyl-4-(3"-trifluoromethylphenoxy)pyrimidine, 2-(2'-chloropyrid-4'-yloxy)-(4"-trifluoromethylphenyl)pyridine, 2-(2'-chloropyrid-4'-yloxy)-6-(3"-trifluoromethylphenyl)pyridine, 2-(3'-chlorophenyl)-5-methyl-4-(1"-methyl-3"-trifluoromethylpyrazol-5"-yloxy)pyrimidine, 2-(3'-chlorophenyl)-5-methyl-4-(3"-trifluoromethylphenoxy)pyrimidine, 2-(4'-fluorophenyl)-6-methyl-4-(3"-trifluoromethylphenoxy) pyrimidine, 2-(4'-fluorophenyl)-4-(1"-methyl-3"-trifluoromethylpyrazol-5"-yloxy)-5-methylpyrimidine, 2-(4'-fluorophenyl)-4-(1"-methyl-3"-trifluoromethylpyrazol-5"-yloxy)-6-methylpyrimidine, 4-(2"-chloropyrid-4"-yloxy)-2-(2',4'-difluorophenyl)-5-methylpyrimidine, 4-(2"-chloropyrid-4"-yloxy)-5,6-dimethyl-2-(4'-trifluoromethoxyphenyl)pyrimidine, 4-(2"-chloropyrid-4"-yloxy)-5,6-dimethyl-2-(4'-trifluoromethylphenyl)pyrimidine, 4-(2"-chloropyrid-4"-yloxy)-5-methyl-2-(4'-trifluoromethoxyphenyl)pyrimidine, 4-(2'-chloropyrid-4"-yloxy)-5-methyl-2-(4'-trifluoromethylphenyl)pyrimidine, 4-(2"-chloropyrid-4"-yloxy)-6-methyl-2-(4'-trifluoromethoxyphenyl)pyrimidine, 4-(2"-chloropyrid-4"-yloxy)-6-methyl-2-(4'-trifluoromethylphenyl)pyrimidine, 4-methyl-6-(4"-trifluoromethoxyphenyl)-2-(1'-methyl-3'-trifluoromethylpyrazol-5'-yloxy)pyridine, 4-methyl-6-(4"-trifluoromethoxyphenyl)-2-(2'-chloropyrid-4'-yloxy)pyridine, 4-methyl-6-(4"-trifluoromethoxyphenyl)-2-(2'-chloropyrid-4'-yloxy) pyridine, 4-methyl-6-(4"-trifluoromethylphenyl)-2-(1'-methyl-3'-trifluoromethylpyrazol-5'-yloxy)pyridine, 4-methyl-6-(4"-trifluoromethylphenyl)-2-(2'-chloropyrid-4'-yloxy)pyridine, 5,6-dimethyl-2-(4'-trifluoromethoxyphenyl)-2-(1"-methyl-3"-trifluoromethylpyrazol-5"-yloxy) pyrimidine, 5,6-dimethyl-2-(4'-trifluoromethoxyphenyl)-4-(3"-trifluoromethylphenoxy)pyrimidine, 5,6-dimethyl-2-(4'-trifluoromethylphenyl)-4-(3"-trifluoromethylphenoxy)pyrimidine, 5,6-dimethyl-4-(1"-methyl-3"-trifluoromethylpyrazol-5"-yloxy)-2-(4'-trifluoromethylphenyl)-pyrimidine, 5-methyl-2-(3'-methylphenyl)-4-(1"-methyl-3"-trifluoromethylpyrazol-5"-yloxy)pyrimidine, 5-methyl-2-(3'-methylphenyl)-4-(3"-trifluoromethylphenoxy)pyrimidine, 5-methyl-2-(4'-trifluoromethoxyphenyl)-2-(1"-methyl-3"-trifluoromethylpyrazol-5"-yloxy)pyrimidine, 5-methyl-2-(4'-trifluoromethoxyphenyl)-4-(3"-trifluoromethylphenoxy)pyrimidine, 5-methyl-2-(4'-trifluoromethylphenyl)-4-(1"-methyl-3"-trifluoromethylpyrazol-5"-yloxy)pyrimidine, 5-methyl-4-(3"-trifluoromethylphenoxy)-2-(4'-trifluoromethylphenoxy)pyrimidine, 6-(4"-fluorophenyl)-2-(1'-methyl-3'-trifluoromethylpyrazol-5'-yloxy)pyridine, 6-methyl-2-(4'-trifluoromethoxyphenyl)-2-(1"-methyl-3"-trifluoromethylpyrazol-5"-yloxy)pyrimidine, 6-methyl-2-(4'-trifluoromethoxyphenyl)-4-(3"-trifluoromethylphenoxy)pyrimidine, 6-methyl-4-(3"-trifluoromethylphenoxy)-2-(4'-trifluoromethylphenyl)pyrimidine, and the like.

The present invention also provides a process for the preparation of a compound of general formula I, which comprises the reaction of a compound of general formula III

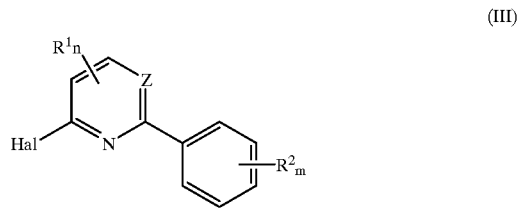

with a compound of general formula IV

A-XM    (IV)

wherein Z, A, $R^1$, $R^2$, m, n and X are as defined hereinbefore; Hal represents a halogen atom; and M represents a metal atom.

The halogen atom Hal may be any halogen atom, suitably a fluorine, chlorine or bromine atom. The metal atom M may be any metal atom, suitably an alkali metal atom such as sodium and potassium.

In practice, the reaction may be carried out in the absence or presence of a solvent which promotes the reaction or at least does not interfere with it. Preferred are polar, aprotic solvents, suitably being N,N-dimethylformamide or dimethylsulfoxide or sulfolane or an ether, such as tetrahydrofurane or dioxane, or mixtures thereof. The reaction is carried out at a temperature between ambient temperature and the reflux temperature of the reaction mixture, preferably at elevated temperature, especially reflux temperature.

Compounds of formula III in which Z is C—H and n is 0 may be obtained by reacting a compound of general formula V

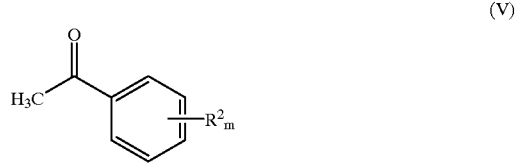

wherein $R^2$ and m are as defined hereinbefore, with an aldehyde, suitably formaldehyde, and a dialkylamine, suitably dimethylamine, according to *Org. Synthesis* Col. Vol. III, 305f, in a solvent, conveniently an alcohol, preferably ethanol, to give a compound of general formula VI,

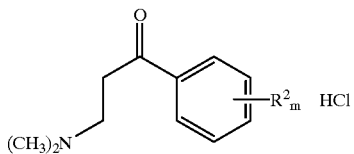
(VI)

which is subsequently reacted according to DBP 21 47 288 (1971) with an ammonium salt, suitably ammonium acetate, and a compound of general formula VII,

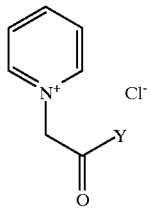
(VII)

wherein Y is an alkoxy group or an $NH_2$-group, preferably an ethoxy group, in a solvent, suitably an alcohol, preferably ethanol, to give a compound of general formula VIII,

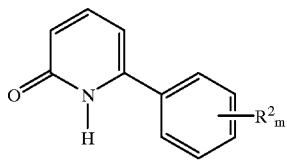
(VIII)

which is further converted by reacting VIII with phosphoryl halogenides (Mücller, E., *Chem. Ber.* 42, 423 (1909); Katritzky et al., *J. Chem. Soc., Perkin Trans.* Part 1, 1980, 2743–2754), preferably phosphoryl bromide or phosphoryl chloride at elevated temperatures, ideally reflux temperature, to give a compound of general formula III.

An alternative, and preferred process for the preparation of compounds of general formula III in which Z is C—H, comprises reacting a 2,6-dihalopyridine of general formula IX

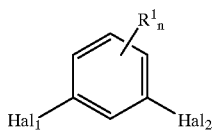
(IX)

wherein $R^1$ and n are as defined hereinbefore, and each $Hal_1$ and $Hal_2$ independently represents a halogen atom, with an in situ prepared metalated benzene derivative of general formula (X) in an approximately equimolar ratio,

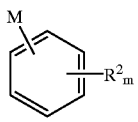
(X)

wherein $R^2$ and m are as defined hereinbefore, and M represents an alkali metal atom.

The alkali metal may be any alkali metal, preferably lithium, and the reaction may be carried out in an aprotic, polar solvent, preferably ethers, to give a compound of general formula III, essentially as disclosed in Cook and Wakefield, *J. Chem. Soc.*, 1969, 2376.

A process for the preparation of compounds of formula III, in which Z represents a nitrogen atom, comprises the reaction of benzamidine hydrochlorides of the general formula XI

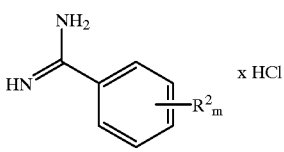
(XI)

wherein $R^2$ and m are as defined hereinbefore with a compound of formula XII,

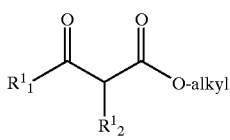
(XII)

wherein each $R^1_1$ and $R^1_2$ independently are as defined hereinbefore; and the O-alkyl group is suitably methoxy or ethoxy, to give a pyrimidinone of general formula XIII.

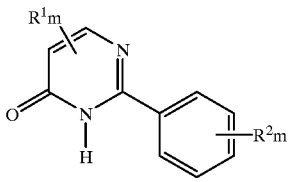
(XIII)

Compounds of general formula XI are known or may be prepared according to procedures described in the art, for example in *Tetrahedron*, 33, 1675f (1979) and *J. Org. Chem.*, 26, 412f. (1960).

The reaction of compounds of formulae XI and XII may be carried out according to *Liebigs Ann.* 1980, 1392f in an organic solvent, suitably an alcohol and preferably ethanol, and in the presence of a base, suitably metal alkoxides, preferably sodium ethoxide.

Compounds of formula XIII may subsequently be converted into compounds of formula III, essentially as described in Davies and Pigott, *J. Chem. Soc.*, 1945, 347, by reaction with a phosphoryl halogenide or thionyl halogenide, preferably phosphoryl chloride, ideally in the absence of a solvent, at elevated temperatures to obtain compounds of formula III.

Compounds of general formula IV are known or may be prepared by known methods. They may be prepared and isolated separately or may be prepared in situ. Generally, a compound of general formula XIV $$A-XH \qquad (XIV)$$

wherein A and X are as hereinbefore defined is reacted with a suitable metal base, for example a metal carbonate or hydride. Preferably the metal salt is a sodium or potassium salt.

Compounds of general formula I may, if desired, be isolated and purified using conventional techniques.

The present invention also provides the use of a compound of general formula I as a herbicide. Further, in accordance with the invention there is provided a method of combating undesired plant growth at a locus by treating the locus with a composition according to the invention or a compound of formula I. The treatment may be a foliar spray application, the locus is most suitably the plants in a crop area, typical crops being cereals, maize, soya bean, sunflower or cotton. However, application may also be to the soil for those compounds having pre-emergence herbicidal action. The dosage of active ingredient used may, for example be in the range of from 0.01 to 10 kg/ha, preferably 0.1 to 1 kg/ha.

The present invention also provides a herbicidal composition which comprises a compound of formula I and at least one carrier.

Preferably there are at least two carriers in a composition of the present invention, at least one of which is a surface-active agent.

A carrier in a composition according to the invention is any material with which the active ingredient is formulated to facilitate application to the locus to be treated, which may be, as appropriate, a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicates such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumaron resins, polyvinyl chloride, and styrene polymers and copolymers; solid polychlorophenols; bitumen; waxes; solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface active agent. For example, the composition may contain at least two carriers, at least one of which is a surface-active agent.

A surface-active agent may be an emulsifying agent, a dispersing agent or a wetting agent; it may be non-ionic or ionic. examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythrol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or earth alkali metal salts, preferably sodium salts, or sulphuric or sulphonic acd esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other active ingredients, for example, compounds possessing insecticidal or fungicidal properties, or other herbicides.

The following examples illustrate the invention. The structures of the compounds prepared in the following examples were additionally confirmed by NMR and mass spectrometry.

EXAMPLES

Example 1

β-Dimethylamino propiophenone hydrochloride

Acetophenone (29.1 ml, 0.25 mol), para-formaldehyde (12.0 g, 0.40 mol) and dimethyl amine hydrochloride (28.5 g, 0.35 mol) are suspended in ethanol (50 ml). Concentrated hydrochloric acid (0.5 ml) is added and the mixture is heated to reflux for 4 h. Then acetone (200 ml) is added and the resulting clear solution is allowed to cool to ambient temperature. The precipitate is collected by filtration and crystallized from ethanol yielding the title compound (40.7 g, 76.0% of theoretical yield) as colorless crystals with mp. 158° C.

Examples 2–4

Additional examples of general formula VI are prepared as exemplified by Example 1. Details are given in Table I

TABLE I (VI)

R²—[phenyl]—C(=O)—CH₂—CH₂—N(CH₃)₂ × HCl

| Ex. No. | R² | mp (° C.) | yield (%) |
|---|---|---|---|
| 2 | 3-trifluoromethyl | 157 | 63 |
| 3 | 2,4-dichloro | 136 | 51 |
| 4 | 2,4-dimethyl | 134 | 72 |

Example 5
6-Phenyl-2-pyridone

Ethyl 2-chloroacetate (10.6 ml, 0.1 mol) is slowly added to hot (105° C.) pyridine (8.9 ml, 0.11 mol whereby the temperature is maintained in the range of 100° C. to 110° C. The resulting brown oil is dissolved in ethanol (60 ml), β-dimethylamino propiophenone hydrochloride (17.7 g, 0.1 mol; prepared according to Example 1) and ammonium acetate (60 g) are added and the mixture is boiled under reflux for 4 h. After cooling, the mixture is filtered and the solvent is evaporated in vacuo. The residue is crystallized from water, collected by filtration and purified by re-crystallization from toluene. The title compound is obtained as colorless crystals (4.7 g, 28% of th.) with mp. 200° C.

Example 6–8

Additional examples are analogously prepared to Example 5. Details are given in Table II.

TABLE II (VII)

| Ex. No. | R² | mp (° C.) | yield (%) |
|---|---|---|---|
| 6 | 3-trifluoromethyl | 174 | 36 |
| 7 | 2,4-dichloro | 255 | 56 |
| 8 | 2,4-dimethyl | 209 | 23 |

Example 9
2-Bromo-6-phenyl pyridine

A mixture of 6-phenyl pyridone (3 g, 17.5 mmol; prepared according to Example 6) and phosphoryl bromide (7.2 g, 25.0 mmol) is heated to 100° C. for 5 h. The cooled mixture is poured into water (40 ml) and the pH is adjusted to 9 by addition of saturated aqueous sodium carbonate. Then the layers are separated and the aqueous layer is extracted with ethyl acetate (50 ml). The combined organic layers are dried with anhydrous magnesium sulphate and the solvent is evaporated in vacuo. The crude product is crystallized from aqueous ethanol. Subsequent purification by flash chromatography (silica gel, hexane/ethyl acetate 9/1 v/v) gives 2-bromo-6-phenyl pyridine (3.1 g, 76% of th.) as light brown crystals with mp 50° C.

Examples 10–12

Additional compounds of general formula III are prepared by procedures analogous to that of Example 9. Details are given in Table III.

TABLE III (III)

| Ex. No. | R² | mp (° C.) | yield (%) |
|---|---|---|---|
| 10 | 3-trifluoromethyl | oil | 82 |
| 11 | 2,4-dichloro | 123 | 88 |
| 12 | 2,4-dimethyl | oil | 68 |

Example 13
2-(1'-Methyl-3'-trifluromethyl pyrazol-5'-yloxy) 6-phenyl pyridine A mixture of 2-bromo-6-phenyl pyridine (0.5 g, 2.1 mmol; prepared according to Example 9), 1-methyl-3-fluoromethyl-5-hydroxypyrazole (0.65 9, 3.9 mmol), potassium carbonate (0.6 g, 4.3 mmol) and N,N-dimethyl formamide (2 ml) are heated to reflux for 12 h. Then the reaction mixture is directly applied onto a flash chromatography column (silica gel). Elution with hexanelethyl acetate (9/1 v/v) gives the title compound (0.35 g, 52.0% of th.) as light-yellow oil.

Examples 14–16

The compounds specified in Table 4 are obtained by procedures analogous to that of Example 13.

TABLE IV (I)

| Ex. No. | A | R² | mp (° C.) | yield (%) |
|---|---|---|---|---|
| 14 | 1'-CH₃-3'-CF₃-pyrazol-5'-yl | 3"-CF₃ | 113 | 93 |
| 15 | 1'-CH₃-3'-CF₃-pyrazol-5'-yl | 2",4"-dichloro | 91 | 78 |
| 16 | 1'-CH₃-3'-CF₃-pyrazol-5'-yl | 2",4"-dimethyl | oil | 95 |

Example 17
2-Fluoro-6-(4'-fluorophenyl)-pyridine

Butyl lithium (105.0 ml, 0.26 mol, 2.5 M solution in hexane) is added to a solution of 1-bromo-4-fluoro benzene (34. 3 ml, 0.31 mol) in anhydrous diethyl ether (200 ml) at −20° C. The mixture is stirred for 60 min and then chilled to −40° C. 2,6-Difluoropyridine (22.7 ml, 0.25 mol) is added and the reaction mixture is allowed to warm to ambient temperature. Subsequently, the mixture is washed with saturated aqueous ammonium chloride (300 ml). The layers are separated and the aqueous layer is washed with diethyl ether 3 times (100 ml each). After drying of the combined organic layers with anhydrous magnesium sulphate, the solvent is removed in vacuo. The crude product is purified by flash column chromatography (silica gel, hexane/AcOEt 8/2) yielding colorless crystals of 2-fluoro-6-(4'-fluorophenyl)-pyridine (19.8 g, 41.0% of th.) with mp 34° C.

Examples 18–19

Analogously to Example 17, the examples of general formula III are prepared as specified in Table V.

TABLE V

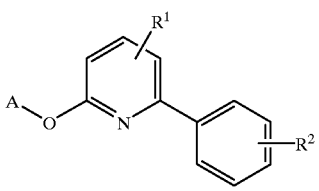

(III)

| Ex. No. | $R^1$ | $R^2$ | mp (° C.) | yield (%) |
|---|---|---|---|---|
| 18 | — | — | oil | 47 |
| 19 | — | 4'-trifluoromethyl | 58 | 75 |
| 20 | — | 3'-trifluoromethyl | oil | 72 |

Example 21

2-(3'-Chlorpyrid-5'-yloxy)-6-(4"-fluorophenvloxy)-pyridine

A mixture of 2-fluoro-6-(4'-fluorophenyl)-pyridine (1.9 g, 10.0 mmol, prepared according to Example 17), 3-chloro-5-hydroxpyridine (1.4 g, 11.0 mmol) and potassium carbonate (1.5 g, 11.0 mmol) in sulfolane (10 ml) is heated to reflux for 8 h. The mixture is allowed to cool to ambient temperature and is then filtered through a bed of silica gel which is subsequently washed with ethyl acetate. The organic solutions are combined and the solvent is evaporated in vacuo. The remaining material is applied onto the top of a flash chromatography column (silica gel) and eluted with hexane/ethyl acetate. Elution with hexanelethyl acetate (8/2 v/v) gives 2-(3'-chlorpyrid-5'-yloxy)-6-(4"-fluorophenyloxy)-pyridine (1.4 g, 46% of th.) as light brown crystals with mp 139° C.

Examples 22–30

Additional compounds are prepared analogously to Example 21. Details are found in Table VI.

TABLE VI (I)

| Ex. No. | $R^1$ | A | $R^2$ | mp (° C.) | yield (%) |
|---|---|---|---|---|---|
| 22 | — | 3'-CF$_3$-phenyl | 4"-fluoro | oil | 48 |
| 23 | — | 2'-chloropyrid-4'-yl | 4"-fluoro | 137 | 37 |
| 24 | — | 2'-chloropyrid-4'-yl | - | 109 | 35 |
| 25 | — | 2'-chloropyrid-4'-yl | 4"-trifluoromethyl | 105 | 51 |
| 26 | — | 1'-CH$_3$-3'-CF$_3$-pyrazol-5'-yl | 4"-fluoro | 87 | 44 |
| 27 | — | 1'-CH$_3$-3'-CF$_3$-pyrazol-5'-yl | 4"-trifluoromethyl | 94 | 59 |
| 28 | — | 1'-CH$_3$-3'-CF$_3$-pyrazol-5'-yl | 3"-trifluoromethyl | 112 | 44 |
| 29 | — | 2'-chloropyrid-4'-yl | 3"-trifluoromethyl | 92 | 54 |
| 30 | — | 2',4'-difluorophenyl | 3"-trifluoromethyl | oil | 72 |

Example 31

4-Fluorobenzmidine hydrochloride

4-Fluorobenzonitrile (10 g, 83 mmol) is dissolved in a mixture of anhydrous ethanol (5 ml) and diethyl ether (70 ml). The reaction mixture is cooled to ice-bath temperature and saturated with gaseous hydrogen chloride for 90 minutes. The mixture is allowed to warm to ambient temperature and stirred overnight.

The colourless precipitates are filtered off, washed with diethyl ether and dissolved in anhydrous ethanol (20 ml). Diethyl ether (100 ml) saturated with gaseous ammonia is added and the solution is stirred for 3 hours.

The resulting suspension filtered and the solvent of the filtrate is removed in vacuo. The residue is washed with diisopropyl ether. After drying colourless crystals (5.15 g, 35.5%) of melting point 210° C. are obtained.

Examples 32 to 37

By method analogous to that of example 31, further compounds of the general formula XI are prepared. Details are given in table VII.

TABLE VII

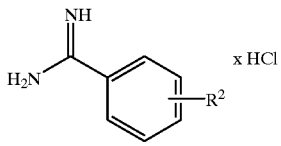

(XI)

| Ex. No. | $R^2$ | mp (° C.) | yield (%) |
|---|---|---|---|
| 32 | 4-trifluoromethyl | 167 | 21.4 |
| 33 | 3-methyl | 243 | 29.7 |
| 34 | 3-chloro | 148 | 17.5 |
| 35 | 3,4-difluoro | 185 | 17.4 |

TABLE VII-continued (XI)

$$\text{H}_2\text{N}-\overset{\text{NH}}{\underset{}{\text{C}}}-\text{C}_6\text{H}_4-\text{R}^2 \cdot x\text{HCl}$$

| Ex. No. | R² | mp (° C.) | yield (%) |
|---|---|---|---|
| 36 | 3-trifluoromethyl | 181 | 17.6 |
| 37 | 3-fluoro | 143 | 20.0 |

Example 38

2-(4'-Fluorophenyl)-5-methyhl-4-pyrimidinone

Sodium hydride (0.52 g, 13 mmol) is added to 20 ml of anhydrous ethanol and stirred for 30 minutes at ambient temperature. To this, 4-fluorobenzamidine hydrochloride (1.47 g, 8.5 mmol) (from example 1) is added and the mixture is stirred for further 30 minutes. Methyl 2-formylpropionate (1 g, 10.6 mmol) is added dropwise and the reaction mixture is left for 4 days under stirring at ambient temperature.

After cooling, the solvent is removed in vacuo and the residue is dissolved in aqueous sodium hydroxide (10 ml, 1M). Then the mixture is brought to pH 5 with 2 molar hydrochloric acid. The precipitate is filtered off and washed with diisopropyl ether. After drying, colourless crystals (0.44 g, 10.3%) of melting point >250° C. are obtained.

Examples 39 to 55

By the method exemplified in example 38, further compounds of the general formula III are prepared. Details are given in table VIII.

TABLE VIII (III)

| Ex. No. | R¹ | R² | mp (° C.) | yield (%) |
|---|---|---|---|---|
| 39 | 6-methyl | 4'-fluoro | 267 | 56.8 |
| 40 | 5-methyl | 4'-trifluoromethyl | >250 | 58.7 |
| 41 | 6-methyl | 4'-trifluoromethyl | 209 | 82.2 |
| 42 | 5-methyl | 3'-methyl | 169 | 34.3 |
| 43 | 6-methyl | 3'-methyl | 185 | 41.6 |
| 44 | 5-methyl | 3'-chloro | 260 | 61.4 |
| 45 | 6-methyl | 3'-chloro | 218 | 51.0 |
| 46 | 5-methyl | 3',4'-difluoro | >250 | 59.4 |
| 47 | 6-methyl | 3',4'-difluoro | 225 | 51.3 |
| 48 | 5-methyl | 3'-trifluoromethyl | 204 | 39.8 |
| 49 | 6-methyl | 3'-trifluoromethyl | 109 | 26.6 |
| 50 | 5,6-dimethyl | 3'-trifluoromethyl | 215 | 70.4 |
| 51 | 5,6-dimethyl | 4'-trifluoromethyl | 242 | 63.5 |
| 52 | 5-methyl | 4'-chloro | >250 | 27.2 |
| 53 | 6-methyl | 4'-chloro | 227 | 6.8 |
| 54 | 5-methyl | 3'-fluoro | 238 | 56.0 |
| 55 | 6-methyl | 3'-fluoro | 194 | 48.4 |

Examples 56

2-(4'-Fluorophenyl)-4-chloro-5-methylpyrimidine

A mixture of 2-(4'-fluorophenyl)-5-methyl-4-pyrimidinone (0.79 g, 3.9 mmol) (from example 5) and phosphorus oxychloride (3 ml) is heated to reflux for 1 hour.

The main excess of phosphorous oxychloride is removed in vacuo and the residue is quenched with water (10 ml) to hydrolyze the remaining reagent. The mixture is neutralized and then extracted with ethyl acetate (50 ml). After drying of the organic layer with anhydrous magnesium sulphate, the solvent is removed in vacuo. The title compound (0.63 g, 72.6%) is obtained as colourless crystals of melting point 133°.

Examples 57–73

The compounds of general formula (XIII) listed in table IX are prepared analogously to the method of example 56.

TABLE IX (III)

| Ex. No. | R¹ | R² | mp (° C.) | yield (%) |
|---|---|---|---|---|
| 57 | 6-methyl | 4'-fluoro | 143 | 97.0 |
| 58 | 6-methyl | 4'-trifluoromethyl | 62 | 71.8 |
| 59 | 5-methyl | 4'-trifluoromethyl | 109 | 87.3 |
| 60 | 5-methyl | 3'-methyl | 154 | 98.8 |
| 61 | 6-methyl | 3'-methyl | 134 | 73.7 |
| 62 | 5-methyl | 3'-chloro | 87 | 94.1 |
| 63 | 6-methyl | 3'-chloro | 101 | 26.1 |
| 64 | 5-methyl | 3',4'-difluoro | 114 | 92.0 |
| 65 | 6-methyl | 3',4'-difluoro | 94 | 90.7 |
| 66 | 5,6-dimethyl | 3'-trifluoromethyl | 83 | 81.6 |
| 67 | 5,6-dimethyl | 4'-trifluoromethyl | 57 | 54.5 |
| 68 | 5-methyl | 3'- | 101 | 81.4 |

TABLE IX-continued (III)

| Ex. No. | R¹ | R² | mp (° C.) | yield (%) |
|---|---|---|---|---|
| 69 | 6-methyl | 3'-trifluoromethyl | 62 | 87.3 |
| 70 | 5-methyl | 4'-chloro | 162 | 85.2 |
| 71 | 6-methyl | 4'-chloro | 101 | 83.6 |
| 72 | 5-methyl | 3'-fluoro | 95 | 83.7 |
| 73 | 6-methyl | 3'-fluoro | 86 | 71.5 |

Example 74

2-(4'-Fluorophenyl)-4-(3"-trifluoromethylphenoxy)-6-methylpyrimidine

A mixture of 2-(4'-fluorophenyl)-4-chloro-6-methylpyridine (0.6 g, 2.7 mmol) (from example 14), a,a,a,-3-hydroxybenzotrifluoride (0.49 g, 3 mmol) and potassium carbonate (0.41 g, 3 mmol) in N,N-dimethylformamide (3 ml) is heated to reflux for 2 hours.

After cooling, ethyl acetate (10 ml) is added and the suspension is filtered through a bed of silica gel using ethyl acetate. The solvent of the filtrate is removed in vacuo and the residue purified by flash silica gel column chromatography using hexane/ethyl acetate 7/2.

Removal of the solvent affords colourless crystals (0.53 g, 56.4%) of melting point 58° C.

Examples 75–97

Further compounds of the general formula I are prepared by the procedure of example 74. Details are given in table X.

TABLE X (I)

| Ex. No. | R¹ | R² | A | mp (° C.) | yield (%) |
|---|---|---|---|---|---|
| 75 | 5-methyl | 4'-fluoro | 1"-CH₃-3"-CF₃-pyrazo(-5"-yloxy | 133 | 54.7 |
| 76 | 6-methyl | 4'-fluoro | 3"-CF₃-phenoxy | 123 | 21.0 |
| 77 | 6-methyl | 4'-CF₃ | 1"-CH₃-3"-CF₃-pyrazol-5"-yloxy | 98 | 39.5 |
| 78 | 6-methyl | 4'-CF₃ | 3"-CF₃-phenoxy | 89 | 79.9 |
| 79 | 5-methyl | 4'-CF₃ | 1"-CH₃-3"-CF₃-pyrazol-5"-yloxy | 147 | 27.6 |
| 80 | 5-methyl | 4'-CF₃ | 3"-CF₃-phenoxy | 95 | 97.6 |
| 81 | 5-methyl | 3'-CH₃ | 1"-CH₃-3"-CF₃-pyrazol-5"-yloxy | 121 | 74.9 |

TABLE X-continued (I)

| Ex. No. | R¹ | R² | A | mp (° C.) | yield (%) |
|---|---|---|---|---|---|
| 82 | 5-methyl | 3'-CH₃ | 3"-CF₃-phenoxy | 71 | 74.5 |
| 83 | 6-methyl | 3'-CH₃ | 1"-CH₃-3"-CF₃-pyrazol-5"-yloxy | 113 | 74.9 |
| 84 | 6-methyl | 3'-CH₃ | 3"-CF₃-phenoxy | 60 | 73.2 |
| 85 | 5-methyl | 3'-chloro | 1"-CH₃-3"-CF₃-pyrazol-5"-yloxy | 116 | 35.4 |
| 86 | 5-methyl | 3'-chloro | 3"-CF₃-phenoxy | 105 | 52.4 |
| 87 | 6-methyl | 3'-chloro | 1"-CH₃-3"-CF₃-pyrazol-5"-yloxy | 96 | 27.1 |
| 88 | 5-methyl | 2',4'-difluoro | 3"-CF₃-phenoxy | 68 | 40.4 |
| 89 | 5-methyl | 2',4'-difluoro | 2"-chloropyrid-4"-yloxy | 146 | 58.8 |
| 90 | 6-methyl | 2',4'-difluoro | 1"-CH₃-3"-CF₃-pyrazol-5"-yloxy | 78 | 56.4 |
| 91 | 6-methyl | 2',4'-difluoro | 3"-CF₃-phenoxy | 64 | 65.3 |
| 92 | 6-methyl | 2',4'-difluoro | 2"-chloropyrid-4"-yloxy | 162 | 31.7 |
| 93 | 5-methyl | 4'-CF₃ | 2"-chloropyrid-4"-yloxy | 99 | 44.1 |
| 94 | 5,6-dimethyl | 4'-CF₃ | 1"-CH₃-3"-CF₃-pyrazol-5"-yloxy | 136 | 13.2 |
| 95 | 5,6-dimethyl | 4'-CF₃ | 3"-CF₃-phenoxy | 73 | 65.6 |
| 96 | 5,6-dimethyl | 3'-CF₃ | 1"-CH₃-3"-CF₃-pyrazol-5"-yloxy | 132 | 30.3 |
| 97 | 5,6-dimethyl | 3'-CF₃ | 3"-CF₃-phenoxy | 105 | 67.5 |

Example 98

Herbicidal Activity

To evaluate their herbicidal activity, compounds according to the invention are tested using a representative range of plants:

| | |
|---|---|
| TRZAS | Triticum aestivum |
| HORVW | Hordeum vulgare |
| GOSHI | Gossypium hirsutum |
| HELAN | Helianthus annuus |
| ORYSA | Oryza sativa |
| GLXMA | Glycine max |
| BEAVA | Beta vulgaris |
| ZEAMX | Zea mays |
| ALOMY | Alopecurus myosuroides |
| AVEFA | Avena fatua |
| ECHCG | Echinocloa crus-galli |
| SETVI | Setaria viridis |
| GALAP | Galium aparine |
| STEME | Stellaria media |
| CHEAL | Chenopodium album |
| VERPE | Veronica persica |
| LAMPU | Lamium purpureum |
| VIOAR | Viola arvensis |
| SIDSP | Sida spinosa |
| AMBAR | Ambrosia artemisifolia |
| ABUTH | Abutilon theophrasti |

-continued

| | |
|---|---|
| IPOPU | Ipomoea purpurea |
| SINAL | Sinapis alba |
| AMARE | Amaranthus retroflexus |

The tests fall into two categories, pre-emergence and post-emergence. The pre-emergence tests involve spraying a liquid formulation of the compound onto the soil in which the seeds of the plant species mentioned above had recently be sown. The post-emergence tests involve spraying seedlings of the above species with a such a formulation.

The soil used in the tests is a prepared horticultural loam. The formulations used in the test are prepared from solutions of the test compounds in acetone containing 0.4% by weight of an alkylphenyl/ethylene oxide condensate surfactant available under the trade mark TRITONx155. The acetone solutions are diluted with water and the resulting formulations at dosage levels corresponding to 1000 g or 300 g of active material per hectare in a volume equivalent to 400 litres per hectare. In the pre-emergence tests untreated sown soil and in the post-emergence tests untreated soil bearing untreated seedling plants are used as controls.

The herbicidal effects of the test compounds are assessed visually twenty days after spraying the foliage and the soil (in the case of examples 13–16 thirteen days after treatment) and are recorded on a 0–9 scale. A rating 0 indicates growth as untreated control, a rating 9 indicates death. An increase of 1 unit on the linear scale approximates to a 10% increase in the level of effect. An asterisk indicates that the specified plant species was not treated in the test.

The results of the test are set out in the table shown below in which the compounds are identified by reference to the preceding examples. An asterisk indicates that the specified plant species was not treated in the test.

| Ex. No | dose g/ha | appl. time | TRZAW | HORVW | GOSHI | HELAN | ORYSA | GLXMA | BEAVA | ZEAMX | ALOMY | AVEFA | ECHCG |
|---|---|---|---|---|---|---|---|---|---|---|---|---|---|
| 13 | 1000 | pre | * | * | * | * | 0 | 0 | 4 | 2 | * | 2 | 4 |
|  |  | post | * | * | * | * | 2 | 5 | 8 | 4 | * | 2 | 5 |
| 14 | 1000 | pre | * | * | * | * | 3 | 4 | 9 | 9 | * | 6 | 8 |
|  |  | post | * | * | * | * | 4 | 6 | 9 | 6 | * | 6 | 7 |
| 15 | 1000 | pre | * | * | * | * | 0 | 2 | 8 | 2 | * | 2 | 5 |
|  |  | post | * | * | * | * | 2 | 6 | 9 | 5 | * | 2 | 7 |
| 16 | 1000 | pre | * | * | * | * | 0 | 0 | 2 | 0 | * | 0 | 2 |
|  |  | post | * | * | * | * | 0 | 2 | 7 | 4 | * | 2 | 2 |
| 21 | 300 | pre | 1 | 0 | 0 | 0 | * | * | * | 0 | 0 | * | * |
|  |  | post | 0 | 0 | 1 | 1 | * | * | * | 1 | 0 | * | * |
| 22 | 300 | pre | 0 | 0 | 0 | 0 | * | * | * | 0 | 0 | * | * |
|  |  | post | 0 | 0 | 1 | 2 | * | * | * | 2 | 0 | * | * |
| 23 | 300 | pre | 1 | 0 | * | 1 | * | * | * | 1 | * | * | * |
|  |  | post | 1 | 2 | * | 3 | * | * | * | 2 | * | * | * |
| 24 | 300 | pre | 0 | 0 | * | 0 | * | * | * | 0 | * | * | * |
|  |  | post | 2 | 2 | * | 3 | * | * | * | 3 | * | * | * |
| 25 | 300 | pre | 0 | 3 | 0 | 0 | * | * | * | 3 | 5 | * | 6 |
|  |  | post | 3 | 3 | 4 | 5 | * | * | * | 4 | 5 | * | 4 |
| 26 | 300 | pre | 0 | 1 | * | 0 | * | * | * | 0 | * | * | * |
|  |  | post | 4 | 3 | * | 4 | * | * | * | 3 | * | * | * |
| 27 | 300 | pre | 4 | 6 | 3 | 3 | * | * | * | 4 | 9 | * | 8 |
|  |  | post | 4 | 5 | 6 | 6 | * | * | * | 4 | 6 | * | 6 |
| 28 | 300 | pre | 1 | 4 | 2 | 0 | * | 3 | * | 1 | 8 | * | 5 |
|  |  | post | 3 | 5 | 8 | 5 | * | 5 | * | 8 | 7 | * | 4 |
| 29 | 300 | pre | 1 | 0 | 0 | 0 | * | 0 | * | 0 | 3 | * | 2 |
|  |  | post | 2 | 2 | 5 | 4 | * | 3 | * | 3 | 3 | * | 2 |
| 30 | 300 | pre | 2 | 0 | 0 | 0 | * | 2 | * | 0 | 0 | * | 0 |
|  |  | post | 0 | 0 | 0 | 0 | * | 0 | * | 0 | 0 | * | 0 |
| 74 | 300 | pre | 0 | 0 | 0 | 0 | * | * | * | 0 | 0 | * | 0 |
|  |  | post | 0 | 0 | 2 | 0 | * | * | * | 0 | 0 | * | 0 |
| 75 | 300 | pre | 3 | 4 | 2 | 1 | * | * | * | 2 | 8 | * | 6 |
|  |  | post | 4 | 5 | 6 | 6 | * | * | * | 4 | 7 | * | 7 |
| 76 | 300 | pre | 1 | 3 | 0 | 0 | * | * | * | 0 | 8 | * | * |
|  |  | post | 3 | 3 | 5 | 5 | * | * | * | 4 | 4 | * | * |
| 77 | 300 | pre | 3 | 5 | 6 | 3 | * | 5 | * | 4 | 9 | * | 8 |
|  |  | post | 4 | 5 | 8 | 8 | * | 8 | * | 5 | 7 | * | 6 |
| 78 | 300 | pre | 3 | 6 | 6 | 2 | * | 3 | * | 3 | 9 | * | 8 |
|  |  | post | 4 | 5 | 8 | 8 | * | 8 | * | 5 | 6 | * | 7 |
| 79 | 300 | pre | 4 | 5 | 8 | 3 | * | 4 | * | 3 | 8 | * | 8 |
|  |  | post | 4 | 5 | 8 | 6 | * | 6 | * | 6 | 8 | * | 5 |
| 80 | 300 | pre | 4 | 7 | 8 | 3 | * | 5 | * | 4 | 8 | * | 8 |
|  |  | post | 4 | 6 | 9 | 8 | * | 8 | * | 6 | 7 | * | 6 |
| 81 | 300 | pre | 0 | 3 | 0 | 0 | 0 | * | 0 | * | 6 | * | 4 |
|  |  | post | 2 | 3 | 4 | 4 | * | 5 | * | 3 | 3 | * | 2 |
| 82 | 300 | pre | 0 | 2 | 0 | 0 | * | 0 | * | 2 | 7 | * | 5 |
|  |  | post | 3 | 3 | 4 | 4 | * | 4 | * | 4 | 4 | * | 3 |
| 83 | 300 | pre | 0 | 0 | 0 | 0 | * | 0 | * | 0 | 3 | * | 4 |
|  |  | post | 0 | 2 | 4 | 4 | * | 3 | * | 2 | 3 | * | 3 |
| 84 | 300 | pre | 0 | 0 | 0 | 0 | * | 0 | * | 0 | 0 | * | 1 |
|  |  | post | 0 | 2 | 0 | 2 | * | 1 | * | 1 | 1 | * | 0 |
| 85 | 300 | pre | 1 | 3 | 2 | 0 | * | 0 | * | 2 | 8 | * | 6 |
|  |  | post | 2 | 4 | 5 | 4 | * | 5 | * | 3 | 5 | * | 4 |

-continued

| | | | | | | | | | | | | | |
|---|---|---|---|---|---|---|---|---|---|---|---|---|---|
| 86 | 300 | pre | 2 | 3 | 2 | 0 | * | 1 | * | 3 | 8 | * | 7 |
| | | post | 3 | 4 | 8 | 4 | * | 5 | * | 5 | 5 | * | 6 |
| 87 | 300 | pre | * | * | * | * | * | * | * | * | * | * | * |
| | | post | * | * | * | * | * | * | * | * | * | * | * |
| 88 | 300 | pre | 0 | 0 | 0 | 0 | * | 0 | * | 0 | 0 | * | 0 |
| | | post | 1 | 1 | 2 | 3 | * | 2 | * | 1 | 1 | * | 2 |
| 89 | 300 | pre | 1 | 3 | 2 | 1 | * | 5 | * | 5 | 5 | * | 6 |
| | | post | 4 | 4 | 6 | 5 | * | 5 | * | 5 | 5 | * | 6 |
| 90 | 300 | pre | 3 | 4 | 3 | 2 | * | 3 | * | 5 | 8 | * | 7 |
| | | post | 4 | 5 | 5 | 5 | * | 6 | * | 5 | 5 | * | 6 |
| 91 | 300 | pre | 0 | 0 | 0 | 0 | * | 0 | * | 0 | 3 | * | 0 |
| | | post | 2 | 2 | 5 | 4 | * | 3 | * | 3 | 3 | * | 3 |
| 92 | 300 | pre | 0 | 0 | 1 | 0 | * | 0 | * | 2 | 2 | * | 0 |
| | | post | 0 | 1 | 4 | 3 | * | 2 | * | 2 | 3 | * | 2 |
| 93 | 300 | pre | 4 | 5 | 7 | 2 | * | 3 | * | 5 | 8 | * | 7 |
| | | post | 5 | 5 | 6 | 5 | * | 5 | * | 6 | 6 | * | 7 |
| 94 | 300 | pre | 3 | 3 | 5 | 4 | * | 3 | * | 3 | 8 | * | 6 |
| | | post | 2 | 4 | 7 | 5 | * | 5 | * | 3 | 5 | * | 5 |
| 95 | 300 | pre | 2 | 5 | 3 | 2 | * | 3 | * | 3 | 7 | * | 6 |
| | | post | 2 | 4 | 6 | 5 | * | 5 | * | 4 | 5 | * | 5 |
| 96 | 300 | pre | 0 | 0 | 2 | 2 | * | 0 | * | 2 | 1 | * | 0 |
| | | post | 1 | 1 | 3 | 4 | * | 2 | * | 1 | 2 | * | 2 |
| 97 | 300 | pre | 0 | 0 | 0 | 0 | * | 3 | * | 0 | 0 | * | 0 |
| | | post | 0 | 1 | 3 | 2 | * | 2 | * | 1 | 0 | * | 1 |

| | SETVI | GALAP | STEME | CHEAL | VERPE | LAMPU | VIOAR | SIDSP | AMBAR | ABUTH | IPOPU | SINAL | AMARE |
|---|---|---|---|---|---|---|---|---|---|---|---|---|---|
| 13 | * | * | * | * | * | * | * | * | * | * | * | 5 | * |
| | * | * | * | * | * | * | * | * | * | * | * | 8 | * |
| 14 | * | * | * | * | * | * | * | * | * | * | * | 8 | * |
| | * | * | * | * | * | * | * | * | * | * | * | 8 | * |
| 15 | * | * | * | * | * | * | * | * | * | * | * | 6 | * |
| | * | * | * | * | * | * | * | * | * | * | * | 6 | * |
| 16 | * | * | * | * | * | * | * | * | * | * | * | 2 | * |
| | * | * | * | * | * | * | * | * | * | * | * | 5 | * |
| 21 | 0 | 0 | 0 | * | 0 | * | 0 | * | * | * | 0 | * | * |
| | 0 | 0 | 0 | * | 0 | * | 0 | * | * | * | 0 | * | * |
| 22 | 1 | 0 | 0 | * | 0 | * | 0 | * | * | * | 0 | * | * |
| | 0 | 0 | 0 | * | 1 | * | 1 | * | * | * | 1 | * | * |
| 23 | 0 | 2 | 0 | 0 | 0 | * | * | * | * | 0 | 0 | * | 0 |
| | 0 | 2 | 4 | 0 | 4 | * | * | * | * | 4 | 1 | * | 5 |
| 24 | 0 | 0 | 0 | 0 | 0 | * | * | * | * | 0 | 0 | * | 0 |
| | 1 | 1 | 2 | 0 | 3 | * | * | * | * | 3 | 2 | * | 4 |
| 25 | 9 | 2 | 7 | * | 9 | 8 | 8 | 4 | 4 | 4 | 2 | * | 9 |
| | 6 | 5 | 4 | * | 6 | * | 6 | 6 | 5 | 4 | 4 | * | 6 |
| 26 | 8 | 0 | 7 | 8 | 8 | * | * | * | * | 0 | 0 | * | 9 |
| | 3 | 3 | 5 | 6 | 8 | * | * | * | * | 5 | 4 | * | 7 |
| 27 | 9 | 6 | 9 | * | 9 | 9 | 8 | 8 | 8 | 6 | 6 | * | 9 |
| | 7 | 5 | 6 | * | 6 | * | 7 | 8 | 5 | 6 | 6 | * | 5 |
| 28 | 9 | 7 | 9 | * | 9 | 9 | 8 | * | * | 8 | 5 | * | 9 |
| | 7 | 6 | 7 | * | 9 | 7 | 8 | * | * | 8 | 6 | * | 7 |
| 29 | 8 | 1 | 6 | * | 8 | 3 | 8 | * | * | 3 | 1 | * | 9 |
| | 4 | 4 | 5 | * | 9 | 5 | 7 | * | * | 4 | 5 | * | 5 |
| 30 | 0 | 0 | 0 | * | 0 | 0 | 0 | * | * | 0 | 5 | * | 0 |
| | 2 | 0 | 0 | * | 0 | 0 | 0 | * | * | 0 | 1 | * | 0 |
| 74 | 0 | 0 | 0 | 6 | 0 | 0 | 0 | 0 | * | 0 | 0 | * | 6 |
| | 1 | 0 | 0 | 0 | 7 | 0 | 0 | 1 | * | 0 | 2 | * | 1 |
| 75 | 9 | 2 | 9 | * | 9 | 9 | 9 | 9 | * | 5 | 3 | * | 9 |
| | 6 | 8 | 7 | * | 9 | 7 | 8 | 6 | * | 6 | 4 | * | 6 |
| 76 | 9 | 5 | 9 | 8 | 9 | 8 | * | 6 | * | 5 | 3 | * | 9 |
| | 6 | 6 | 8 | 9 | 9 | 8 | * | 6 | * | 6 | 4 | * | 6 |
| 77 | 9 | 8 | 9 | * | 9 | 9 | 8 | * | * | 8 | 9 | * | 9 |
| | 8 | 7 | 8 | * | 9 | 8 | 9 | * | * | 8 | 7 | * | 8 |
| 78 | 9 | 8 | 9 | * | 9 | 8 | 8 | * | * | 9 | 9 | * | 9 |
| | 9 | 7 | 8 | * | 9 | 8 | 8 | * | * | 8 | 8 | * | 7 |
| 79 | 9 | 8 | 9 | * | 9 | 8 | 8 | * | * | 9 | 9 | * | 9 |
| | 8 | 7 | 8 | * | 9 | 8 | 8 | * | * | 8 | 8 | * | 7 |
| 80 | 9 | 8 | 9 | * | 9 | 9 | 8 | * | * | 9 | 9 | * | 9 |
| | 8 | 7 | 8 | * | 8 | 8 | 8 | * | * | 8 | 8 | * | 8 |
| 81 | 9 | 0 | 6 | * | 9 | 8 | 7 | * | * | 2 | 4 | * | 8 |
| | 8 | 3 | 4 | * | 9 | 7 | 5 | * | * | 4 | 5 | * | 5 |
| 82 | 9 | 1 | 5 | * | 9 | 6 | 8 | * | * | 4 | 4 | * | 9 |
| | 4 | 4 | 4 | * | 9 | 5 | 7 | * | * | 4 | 5 | * | 7 |
| 83 | 7 | 1 | 2 | * | 8 | 3 | 7 | * | * | 1 | 2 | * | 9 |
| | 4 | 3 | 3 | * | 9 | 4 | 5 | * | * | 2 | 4 | * | 5 |
| 84 | 0 | 0 | 0 | * | 0 | 0 | 2 | * | * | 0 | 0 | * | 0 |
| | 1 | 2 | 2 | * | 3 | 1 | 5 | * | * | 1 | 3 | * | 4 |
| 85 | 9 | 6 | 9 | * | 8 | 8 | 8 | * | * | 5 | 5 | * | 9 |

-continued

|    |   |   |   |   |   |   |   |   |   |   |   |   |   |
|----|---|---|---|---|---|---|---|---|---|---|---|---|---|
|    | 5 | 6 | 4 | * | 9 | 8 | 7 | * | * | 5 | 4 | * | 5 |
| 86 | 9 | 3 | 8 | * | 9 | 7 | 8 | * | 5 | 4 | * | 9 |   |
|    | 7 | 6 | 5 | * | 9 | 7 | 8 | * | * | 4 | 5 | * | 6 |
| 87 | * | * | * | * | * | * | * | * | * | * | * | * | * |
|    | * | * | * | * | * | * | * | * | * | * | * | * | * |
| 88 | 0 | 0 | 0 | * | 2 | 2 | 4 | * | * | 0 | 0 | * | 4 |
|    | 2 | 3 | 4 | * | 5 | 3 | 5 | * | * | 2 | 6 | * | 4 |
| 89 | 8 | 3 | 9 | * | 9 | 8 | 9 | * | * | 7 | 9 | * | 9 |
|    | 7 | 4 | 5 | * | 9 | 6 | 8 | * | * | 6 | 7 | * | 6 |
| 90 | 9 | 4 | 9 | * | 9 | 9 | 9 | * | * | 9 | 7 | * | 9 |
|    | 7 | 5 | 6 | * | 9 | 6 | 8 | * | * | 5 | 7 | * | 6 |
| 91 | 9 | 1 | 7 | * | 8 | 4 | 8 | * | * | 2 | 3 | * | 9 |
|    | 3 | 4 | 4 | * | 9 | 5 | 8 | * | * | 4 | 6 | * | 5 |
| 92 | 8 | 0 | 7 | * | 7 | 3 | 8 | * | * | 2 | 4 | * | 8 |
|    | 4 | 3 | 5 | * | 6 | 4 | 8 | * | * | 4 | 6 | * | 6 |
| 93 | 9 | 5 | 9 | * | 9 | 9 | 9 | * | * | 9 | 9 | * | 9 |
|    | 7 | 6 | 6 | * | 9 | 6 | 8 | * | * | 6 | 8 | * | 7 |
| 94 | 9 | 5 | 9 | * | 9 | 9 | 9 | * | * | 9 | 9 | * | 9 |
|    | 6 | 5 | 5 | * | 9 | 6 | 8 | * | * | 6 | 9 | * | 6 |
| 95 | 9 | 4 | 9 | * | 9 | 6 | 9 | * | * | 7 | 6 | * | 8 |
|    | 7 | 5 | 6 | * | 8 | 6 | 8 | * | * | 5 | 9 | * | 6 |
| 96 | 8 | 0 | 4 | * | 7 | 0 | 8 | * | * | 0 | 5 | * | 8 |
|    | 2 | 4 | 4 | * | 7 | 4 | 7 | * | * | 4 | 5 | * | 4 |
| 97 | 3 | 0 | 0 | * | 0 | 0 | 3 | * | * | 0 | 3 | * | 5 |
|    | 2 | 3 | 3 | * | 4 | 3 | 5 | * | * | 2 | 5 | * | 5 |

We claim:
1. A compound of the general formula I

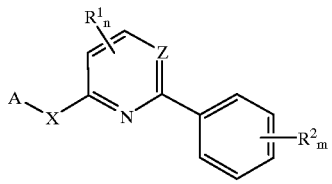

(I)

wherein
Z represents a C—H group;
A represents an optionally substituted 5- or 6-membered nitrogen-containing heteroaromatic group selected from pyrazolyl, imidazolyl, triazolyl, tetrazolyl, pyridyl, pyrazinyl, pyridazinyl and triazinyl, wherein the heteroaromatic groups are optionally substituted by one or more of the same or different substitutents selected from halogen, nitro, cyano, amino, hydroxyl, C1–4-alkyl, C1–4-alkoxy, C1–4-haloalkyl, C1–4-haloalkoxy and halosulphonyl groups;
n represents an integer from 0 to 2 and $R^1$ or each $R^1$ independently represents a hydrogen atom or an optionally substituted alkyl, alkoxy, alkylthio or dialkylamino group;
m represents an integer from 0 to 5 and $R^2$ or each $R^2$ independently represents a hydrogen or a halogen atom or an optionally substituted alkyl, haloalkyl, haloalkoxy, alkoxy, alkylthio group or a nitro, cyano or a halosulphanyl group; and
X represents an oxygen or sulphur atom;
with the proviso that when
Z represents a C—H group, A represents a 1-methyl-3-trifluoromethyl-pyrazol-5-yl group,
n is 0 and X represents an oxygen atom, then
m must be other than 0, and when m is 1 then
$R^2$ cannot be a 3-trifluoromethyl substituent and when m is 2
then $R^2$ cannot be a 2,4 dichloro substituent or a 2,4 dimethyl substitutent.

2. A compound as claimed in claim 1 wherein
A represents a pyridyl or pyrazolyl group being substituted by one or more of the same or different substituents selected from halogen atoms, alkyl groups, alkoxy groups, haloalkyl groups, haloalkoxy groups and pentahalosulphonyl groups.

3. A compound as claimed in claim 2 wherein
A has a substituent in the meta-position relative to the point of attachment.

4. A compound as claimed in claim 3 wherein
A is meta-substituted by a chlorine atom or a trifluoromethyl group.

5. A compound as claimed in claim 1 wherein
X is oxygen.

6. A compound as claimed in claim 1 selected from the group consisting of:
2-(1'-methyl-3'-trifluoromethylpyrazol-5'-yloxy)-6-(4"-trifluoromethylphenyl)pyridine,
2-(2'-chloropyrid-4'-yloxy)-(4"-trifluoromethylphenyl)pyridine,
2-(2'-chloropyrid-4'-yloxy)-6-(3"-trifluoromethylphenyl)pyridine,
4-methyl-6-(4"-trifluoromethoxyphenyl)-2-(1'-methyl-3'-trifluoromethylpyrazol-5'-yloxy)pyridine,
4-methyl-6-(4"-trifluoromethoxyphenyl)-2-(2'-chloropyrid-4'-yloxy)pyridine,
4-methyl-6-(4"-trifluoromethylphenyl)-2-(1'-methyl-3'-trifluoromethylpyrazol-5'-yloxy)pyridine,
4-methyl-6-(4"-trifluoromethylphenyl)-2-(2'-chloropyrid-4'-yloxy)pyridine, and
6-(4"-fluorophenyl)-2-(1'-methyl-3'-trifluoromethylpyrazol-5'-yloxy)pyridine.

7. A herbicidal composition which comprises at least one compound of formula I as defined in claim 1 and a carrier and/or a surface-active agent.

8. A method of combating undesired plant growth at a locus, which comprises treating the locus with at least one compound of formula I as defined in claim 1.